United States Patent
Sharma et al.

(10) Patent No.: US 10,485,901 B2
(45) Date of Patent: Nov. 26, 2019

(54) IMPLANT WITH REACTIVE OXYGEN SPECIES SCAVENGING COATING

(71) Applicant: BATTELLE MEMORIAL INSTITUTE, Columbus, OH (US)

(72) Inventors: Gaurav Sharma, Lewis Center, OH (US); Ramanathan S. Lalgudi, Westerville, OH (US); Chad E. Bouton, Powell, OH (US)

(73) Assignee: BATTELLE MEMORIAL INSTITUTE, Columbus, OH (US)

( * ) Notice: Subject to any disclaimer, the term of this patent is extended or adjusted under 35 U.S.C. 154(b) by 19 days.

(21) Appl. No.: 15/807,979

(22) Filed: Nov. 9, 2017

(65) Prior Publication Data

US 2018/0078681 A1    Mar. 22, 2018

Related U.S. Application Data

(62) Division of application No. 15/053,532, filed on Feb. 25, 2016, now abandoned.

(60) Provisional application No. 62/121,177, filed on Feb. 26, 2015.

(51) Int. Cl.
   *A61L 31/10* (2006.01)
   *A61N 1/05* (2006.01)

(52) U.S. Cl.
   CPC ............ *A61L 31/10* (2013.01); *A61N 1/0536* (2013.01); *A61L 2400/18* (2013.01)

(58) Field of Classification Search
   None
   See application file for complete search history.

(56) References Cited

U.S. PATENT DOCUMENTS

| | | | |
|---|---|---|---|
| 5,368,931 A * | 11/1994 | Kato | C08F 2/08 101/457 |
| 6,350,368 B1 | 2/2002 | Willner et al. | |
| 6,500,857 B1 * | 12/2002 | Perricone | A61K 8/0208 424/401 |
| 8,454,820 B2 | 6/2013 | Aoki et al. | |
| 8,929,968 B2 | 1/2015 | Brister et al. | |
| 2006/0121089 A1 * | 6/2006 | Michal | A61K 31/337 424/426 |
| 2007/0198080 A1 * | 8/2007 | Ding | A61L 31/10 623/1.38 |
| 2010/0239635 A1 | 9/2010 | McClain et al. | |

(Continued)

FOREIGN PATENT DOCUMENTS

WO   WO-2011144650 A1 * 11/2011   ........... A61K 31/167

OTHER PUBLICATIONS

GC McConnell, HD Rees, AL Levey, C-A Gutekunst, RE Gross, RV Bellamkonda. "Implanted neural electrodes cause chronic, local inflammation that is correlated with local neurodegeneration." Journal of Neural Engineering, vol. 6, 2009, pp. 1-12. (Year: 2009).*

(Continued)

*Primary Examiner* — Isaac Shomer
(74) *Attorney, Agent, or Firm* — Fay Sharpe LLP

(57) ABSTRACT

A chronically implanted medical device is disclosed that has an outermost layer formed from a conjugate of a polymer with lipoic acid, the conjugate having free 1,2-dithiolane groups. It is contemplated that this layer scavenges reactive oxygen species, i.e. acts as an antioxidant, and thus reduces inflammation and other adverse effects around the implant itself.

20 Claims, 2 Drawing Sheets

(56) References Cited

U.S. PATENT DOCUMENTS

2010/0298908 A1* 11/2010 Vardiman ............ A61N 1/0534
607/45
2012/0073897 A1 3/2012 Ohnishi et al.

OTHER PUBLICATIONS

RF Enes, ASF Farinha, AC Tome, JAS Cavaleiro, R Amorati, S Petrucci, GF Pedulli. "Synthesis and antioxidant activity of [60] fullerene—flavonoid conjugates." Tetrahedron, vol. 65, 2009, pp. 253-262. (Year: 2009).*

RF Enes, AC Tome, JAS Cavaleiro, R Amorati, MG Fumo, GF Pedulli, L Valgimigli. "Synthesis and Antioxidant Activity of [60] Fullerene—BHT Conjugates." Chemistry A European Journal, vol. 12, 2006, pp. 4646-4653. (Year: 2006).*

Chekmeneva et al.; Complexation of $Hg^{2}+$ with α-Lipoic and Dihydrolipoic Acids: Study by Differential Pulse Voltammetry on Rotating Au-Disk Electrode and ESI-MS; Electroanalysis; 2010; pp. 177-184; 22 No. 2.

Lee et al.; Fabrication of an adipoic acid-eluting poly-(D,L-lactide-co-caprolactone) cuff for the inhibition of neointimal formation; Experimental and Molecular Medicine; Jan. 2009; pp. 25-32; vol. 41, No. 1.

Rao et al.; Polyethylene glycol-containing polyurethane hydrogel coatings for improving the biocompatibility of neural electrodes; Acta Biomaterialia 8; 2012; pp. 2233-2242.

Yoshitomi et al.; Creation of a blood-compatible surface: a novel strategy for suppressing blood activation and coagulation using a nitroxide radical-containing polymer with reactive oxygen species scavenging activity; Acta Biomaterialia 8; 2012; pp. 1323-1329.

R Wel, L Cheng, M Zheng, R Cheng, F Meng, C Deng, Z Zhong "Reduction-Responsive Disassemblable Core-Cross-Linked Micelles Based on Poly(ethylene glycol)-b-poly(N-2-hydroxypropyl rnethacrylamide)-Lipoic Acid Conjugates for Triggered Intracellular Anticancer Drug Release." Biomacromolecules, vol. 13, 2012, 2429-2438.

* cited by examiner

IMPLANT WITH REACTIVE OXYGEN SPECIES SCAVENGING COATING

CROSS-REFERENCE TO RELATED APPLICATIONS

This application is a divisional of U.S. patent application Ser. No. 15/053,532, filed Feb. 25, 2016, which claims priority to U.S. Provisional Patent Application Ser. No. 62/121,177, filed Feb. 26, 2015. That application is hereby fully incorporated by reference in its entirety.

BACKGROUND

The present disclosure relates to methods of reducing inflammation around a chronically implanted medical device by coating the device with a polymer/lipoic acid conjugate. This conjugate is particularly useful for coating an electrode which is inserted into the brain, as neurodegeneration around the electrode is reduced, thus permitting neural signals to be recorded by the electrode for an extended period of time.

Neural signal recording failure from chronically implanted neural electrodes is a major issue that limits the widespread deployment of such devices for rehabilitation related applications where the recording of brain signals is useful or necessary. It is widely hypothesized that glial scar, which is a result of the body's immune response to the "foreign" electrodes, electrically impedes the recording ability of the electrodes.

Recently, it has been suggested that the presence of electrodes in brain tissue creates a chronic inflammatory state which causes neurodegeneration (loss of neuron function) and can lead to implant failure. Reactive oxygen species (ROS) such as hydroxyl and superoxide radicals may play an important role in the initiation and progression of chronic inflammation around the electrodes.

It would be desirable to reduce inflammation and neurodegeneration around chronically implanted devices, such as electrodes, in the brain. More generally, reducing inflammation around a chronically implanted medical device may be desirable as well.

BRIEF DESCRIPTION

The present disclosure relates to processes and methods for reducing inflammation and neurodegeneration. Briefly, a chronically implanted medical device, such as an electrode, is coated with a polymer conjugate. The polymer conjugate is formed from a polymer and lipoic acid. The resulting conjugate contains free 1,2-dithiolane groups from the lipoic acid, or in other words it is the carboxylic acid portion of the lipoic acid that forms a covalent bond with the polymer.

Disclosed in various embodiments are implantable devices, comprising: a substrate having a surface; and an outermost layer on the surface comprising a conjugate of a polymer with lipoic acid, the conjugate containing free 1,2-dithiolane groups. In specific embodiments, the device can be an electrode.

The polymer may contain sidechains having a terminal epoxy, hydroxyl, or amino group which react with the lipoic acid. The polymer may be a copolymer. The polymer may be formed from a first monomer selected from the group consisting of silanes, acrylates, acrylamides, and vinylphenols. The second monomer may be an alkene. In particular embodiments, the polymer is a poly(glycidyl methacrylate) polymer.

In the conjugate of the polymer with lipoic acid, the lipoic acid generally reacts with a reactive sidechain and forms a covalent bond. As a result, the conjugate may be considered a copolymer as well.

Also disclosed are methods of reducing neurodegeneration around an electrode in a patient, comprising: inserting an electrode into a patient, the electrode having an outermost coating comprising a conjugate of a polymer with alpha lipoic acid, the conjugate containing free 1,2-dithiolane groups.

In some embodiments, the methods further comprise: inserting a separate stimulating electrode into the patient proximate to the electrode having the outermost coating; and sending an electrical signal to the stimulating electrode to enable redox chemistry at the electrode having the outermost coating.

The electrode can be inserted into the brain of the patient.

Also described herein are methods of reducing inflammation around an implanted medical device, comprising: coating the medical device with an outermost layer comprising a conjugate of a polymer with alpha lipoic acid, the conjugate containing free 1,2-dithiolane groups. The coated medical device, when implanted, should suffer less inflammation in the region proximate the medical device due to the coating.

Also disclosed in embodiments herein are graft copolymers formed from the reaction of: a polymer having a silane backbone or having epoxy sidechains; and lipoic acid. In specific varieties, the polymer is a poly(glycidyl methacrylate) polymer These and other non-limiting characteristics are more particularly described below.

BRIEF DESCRIPTION OF THE DRAWINGS

The following is a brief description of the drawings, which are presented for the purposes of illustrating the exemplary embodiments disclosed herein and not for the purposes of limiting the same.

DETAILED DESCRIPTION

Figure 1:
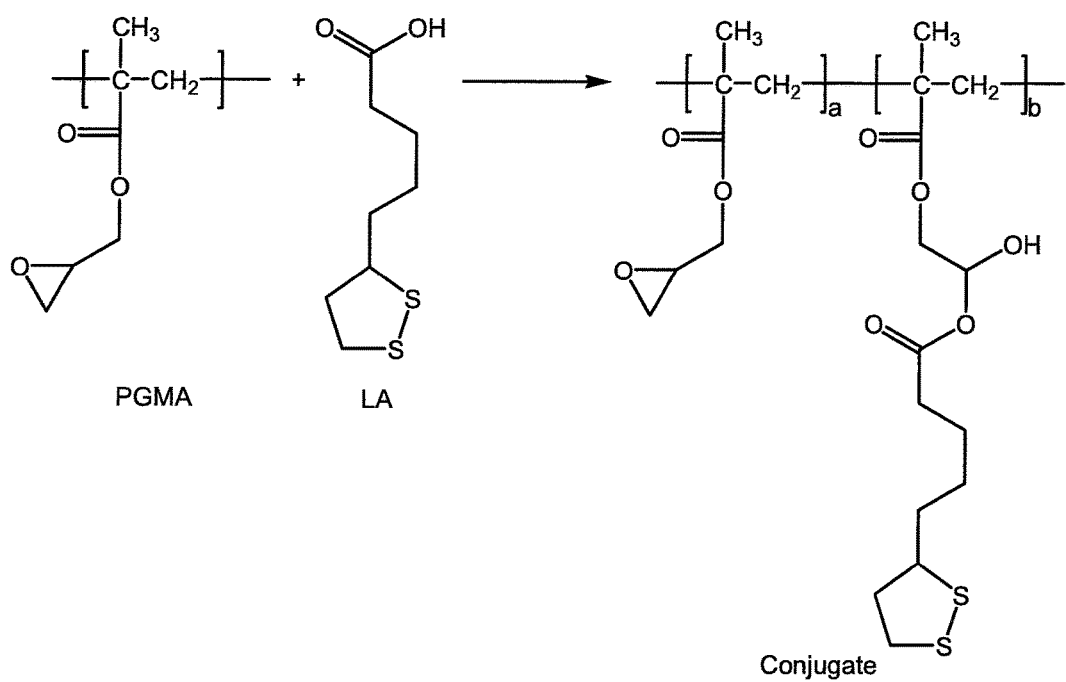
FIG. 1 is an illustration of the formation of a polymer/lipoic acid conjugate of the present disclosure.

The present disclosure may be understood more readily by reference to the following detailed description of desired embodiments and the examples included therein. In the following specification and the claims which follow, reference will be made to a number of terms which shall be defined to have the following meanings.

Although specific terms are used in the following description for the sake of clarity, these terms are intended to refer only to the particular structure of the embodiments selected for illustration in the drawings, and are not intended to define or limit the scope of the disclosure. In the drawings and the following description below, it is to be understood that like numeric designations refer to components of like function. Furthermore, it should be understood that the drawings are not to scale.

The singular forms "a," "an," and "the" include plural referents unless the context clearly dictates otherwise.

The term "comprising" is used herein as requiring the presence of the named components/steps and allowing the presence of other components/steps. The term "comprising"

should be construed to include the term "consisting of", which allows the presence of only the named components/steps, along with any impurities that might result from the manufacture of the named components/steps.

Numerical values should be understood to include numerical values which are the same when reduced to the same number of significant figures and numerical values which differ from the stated value by less than the experimental error of conventional measurement technique of the type described in the present application to determine the value.

All ranges disclosed herein are inclusive of the recited endpoint and independently combinable (for example, the range of "from 2 grams to 10 grams" is inclusive of the endpoints, 2 grams and 10 grams, and all the intermediate values).

The term "about" can be used to include any numerical value that can vary without changing the basic function of that value. When used with a range, "about" also discloses the range defined by the absolute values of the two endpoints, e.g. "about 2 to about 4" also discloses the range "from 2 to 4." The term "about" may refer to plus or minus 10% of the indicated number.

The term "alkene" refers to a molecule composed entirely of carbon atoms and hydrogen atoms which contains at least one carbon-carbon double bond that is not part of an aryl or heteroaryl structure. The alkene molecule may be linear or branched. Exemplary alkenes include ethylene and propylene.

The term "hydroxyl" refers to a radical of the formula —OH, wherein the oxygen atom is covalently bonded to a carbon atom The terms "carboxy" or "carboxyl" refers to a radical of the formula —COOH, wherein the carbon atom is covalently bonded to another carbon atom. It should be noted that for the purposes of this disclosure, a carboxyl group may be considered as having a hydroxyl group. However, it should be noted that a carboxyl group can participate in certain reactions differently from a hydroxyl group.

The term "amino" refers to a radical of the formula $R_1$—$NHR_2$, wherein $R_1$ is a carbon atom, and $R_2$ is a carbon atom or a hydrogen atom. For purposes of this disclosure, an amino group is a primary amino group or a secondary amino group, and can be reacted.

The present disclosure relates to a graft copolymer that acts as a scavenger of reactive oxygen species (ROS). The graft copolymer is formed by conjugating a polymer with lipoic acid, where the 1,2-dithiolane group of the lipoic acid remains free. This graft copolymer is applied as a coating to a medical device, such as an electrode.

Lipoic acid (LA) and its redox couple, dihydrolipoic acid (DHLA), are depicted below:

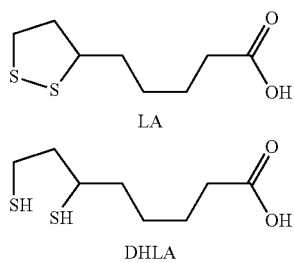

Lipoic acid (LA, thioctic acid, 1,2-dithiolane-3-pentanoic acid) and DHLA both act as antioxidants by reacting with ROS such as hydrogen peroxide, hydroxyl radicals, singlet oxygen, hypochlorous acid (HOCl), peroxynitrite ($ONOO^-$), and superoxide radicals. They can also recycle/regenerate other antioxidants such as vitamin C, thioredoxin, and glutathione, which in turn can recycle vitamin E.

Microglia form the first layer of cells that surround the neural electrode. Microglia are macrophage-type cells that secrete ROS and cytokines. These in turn attract other cells, such as astrocytes, to the electrodes and thus lead to the formation of glial scar around the neural electrodes. As a result, the same signal to be read by the electrode changes over time.

Placing a coating of LA/DHLA on the surface of the implanted electrode is contemplated to provide rapid scavenging of ROS in the immediate vicinity of the electrode, thus reducing the immune response. Thus, an electrode, or generally any medical device intended to be chronically implanted, can be coated so that its outermost surface is formed from the polymer conjugate/graft copolymer of the present disclosure.

In addition, LA/DHLA form a redox pair. The reduction potential for the LA/DHLA couple is reported to be between −320 mV and −290 mV. LA can accept electrons and be reduced to DHLA, while DHLA can react with a free radical and be oxidized back to LA. Thus, it is possible to regenerate the desired form of LA/DHLA using stimulating electrodes that provide/remove electrons as needed, or by using the same electrode upon which the LA/DHLA is coated. For purposes of this disclosure, any reference to lipoic acid should be construed as also referring to dihydrolipoic acid.

The coating/outermost layer is formed from a conjugate of a polymer with lipoic acid. This polymer conjugate can also be considered a graft copolymer. The conjugate is formed by the reaction of the polymer with lipoic acid.

Generally, the polymer contains sidechains that can react with the carboxyl group of lipoic acid. The sidechains include a terminal epoxy group, hydroxyl group, or amino group, all of which can react with a carboxyl group. In particular, the reaction of a carboxyl group with a hydroxyl group will result in an ester linkage, while the reaction of a carboxyl group with an amino group will result in an amide linkage.

The polymer can be a homopolymer, or can be a copolymer formed from two or more monomers. In particular embodiments, the polymer can be formed from a first monomer selected from the group consisting of acrylates, acrylamides, silanes, and vinylphenols. If the polymer is a copolymer, the second monomer can be another one of the first monomers, or can be an alkene such as ethylene, propylene, etc.

Acrylate monomers contain a vinyl group directly attached to a carbonyl carbon, where the carbonyl and a reactive hydroxyl group. Exemplary acrylate monomers include acrylic acid, methyl acrylate, methyl methacrylate, ethyl acrylate, butyl acrylate, 2-ethylhexyl acrylate, hydroxyethyl methacrylate, butyl acrylate, and butyl methacrylate. Acrylamides contain a vinyl group and an amide group. An exemplary acrylamide is prop-2-enamide. Silane monomers can be used to form a silane coating on the substrate and also provide a terminal sidechain group for the lipoic acid to react with. Exemplary silanes can include trimethoxy[3-(methylamino)propyl]silane or 3-hydroxypropyltrimethoxysilane, which can be used to form siloxane polymers. Other monomers that might be suitable for producing the polymer include vinyl alcohol and ethylene imine.

In more specific embodiments, the polymer that is used to form the conjugate includes a terminal epoxy group which is reacted with the carboxyl group of the lipoic acid. In particular embodiments, the polymer is poly(glycidyl methacrylate), herein abbreviated as PGMA. FIG. 1 is a depiction of a chemical reaction showing how the conjugate is formed by the reaction of a PGMA homopolymer with lipoic acid (LA) to obtain a graft copolymer. The two monomers of the conjugate reflect the fact that the LA does not react with all epoxy groups of the PGMA homopolymer. The molar ratio of monomers that have not reacted to monomers that have reacted is indicated by a:b. The ratio of a:b can range from 1:99 to 99:1, and is desirably 50:50 or higher (with more LA sidechain being preferred).

More generally, the polymer conjugate of the present disclosure can be represented by Formula (I) below:

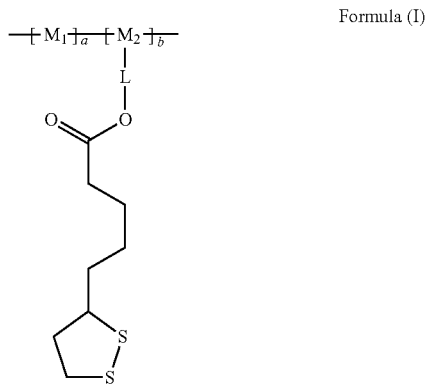

Formula (I)

where $M_1$ and $M_2$ are independently a monomer; L is a divalent linking group; and a and b represent the molar percentage of each monomer present in the polymer conjugate, where a+b=100 molar percent. It is noted that the 1,2-dithiolane group of the LA is free at the end of the sidechain, and is able to react with ROS.

Figure 2:
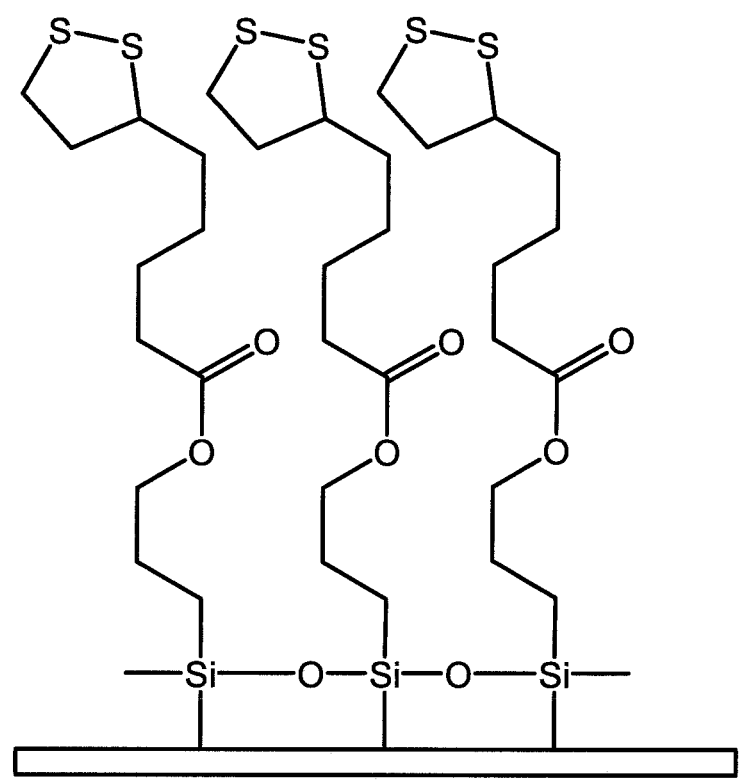
FIG. 2 is an illustration of the formation of a polymer/lipoic acid conjugate, where the polymer is a siloxane, and the substrate is shown.

FIG. 2 is an illustration of a substrate upon which is a conjugate formed from a siloxane polymer having LA conjugated therefrom.

As previously mentioned, LA/DHLA form a redox pair. More generally, the present disclosure can be considered to be directed to the use of a conjugate of a polymer with any molecule that forms a redox pair and can scavenge reactive oxygen species. Lipoic acid and dihydrolipoic acid are one example of such a molecule.

The following examples are provided to illustrate the devices, polymer conjugates, and methods of the present disclosure. The examples are merely illustrative and are not intended to limit the disclosure to the materials, conditions, or process parameters set forth therein.

EXAMPLES 1 gram of poly(glycidyl methacrylate) (PGMA) was dissolved in 10 mL of dimethyl sulfoxide in a 3 neck round bottom flask fitted with a magnetic stirrer, gas inlet, and a condenser. Once the polymer was dissolved, 0.25 grams of lipoic acid and 0.03 grams of t-butyl ammonium bromide (catalyst) were added and stirred at room temperature for 24 hours under an inert argon atmosphere. The product obtained was precipitated from methanol and dried in vacuum oven at a temperature of 40° C. for 24 hours. The product was characterized by acid value titration. 48% of the starting 0.25 grams of lipoic acid was found to be grafted onto the PGMA.

The present disclosure has been described with reference to exemplary embodiments. Obviously, modifications and alterations will occur to others upon reading and understanding the preceding detailed description. It is intended that the present disclosure be construed as including all such modifications and alterations insofar as they come within the scope of the appended claims or the equivalents thereof.

The invention claimed is:

1. A method of reducing neurodegeneration around an electrode in a patient, comprising: inserting an electrode into a patient, the electrode having an outermost coating comprising a conjugate of a polymer with alpha lipoic acid, the conjugate containing free 1,2-dithiolane groups;

inserting a separate stimulating electrode into the patient proximate to the electrode having the outermost coating; and sending an electrical signal to the stimulating electrode to regenerate the conjugate.

2. The method of claim 1, wherein an electrical signal is sent to the electrode to provide electrons for regenerating the conjugate.

3. The method of claim 1, wherein the electrode is inserted into the brain of the patient.

4. The method of claim 1, wherein the polymer contains sidechains having a terminal epoxy, hydroxyl, or amino group which react with lipoic acid.

5. The method of claim 1, wherein the polymer includes a first monomer selected from the group consisting of acrylates, acrylamides, silanes, and vinylphenols.

6. The method of claim 5, wherein the polymer includes a second monomer which is an alkene.

7. The method of claim 1, wherein the polymer is a poly(glycidyl methacrylate) polymer.

8. The method of claim 1, wherein the conjugate has the structure of Formula (I):

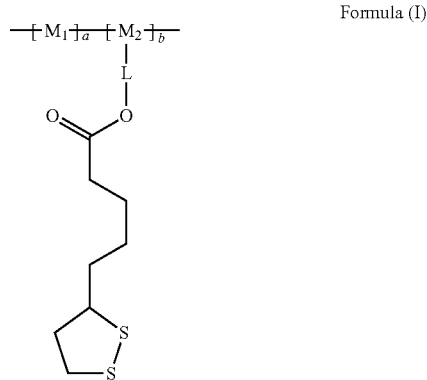

Formula (I)

where $M_1$ and $M_2$ are independently a monomer; L is a divalent linking group; and a and b represent the molar percentage of each monomer present in the polymer conjugate, where a+b=100 molar percent.

9. A method of reducing inflammation around an implanted medical device, comprising: coating the medical device with an outermost layer comprising a conjugate of a polymer with alpha lipoic acid, the conjugate containing free 1,2-dithiolane groups;

wherein the conjugate has the structure of Formula (I):

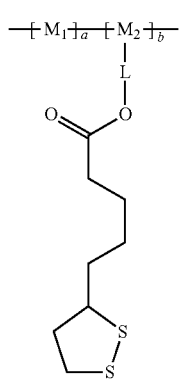

Formula (I)

where $M_1$ and $M_2$ are independently a monomer; L is a divalent linking group; and a and b represent the molar percentage of each monomer present in the polymer conjugate, where a+b=100 molar percent.

10. The method of claim 9, wherein the polymer contains sidechains having a terminal epoxy, hydroxyl, or amino group which react with lipoic acid.

11. The method of claim 9, wherein the polymer includes a first monomer selected from the group consisting of acrylates, acrylamides, silanes, and vinylphenols.

12. The method of claim 11, wherein the polymer includes a second monomer which is an alkene.

13. The method of claim 9, wherein the polymer is a poly(glycidyl methacrylate) polymer.

14. A method of reducing neurodegeneration around an electrode in a patient, comprising: inserting an electrode into a patient, the electrode having an outermost coating comprising a conjugate of a polymer with a molecule, wherein the molecule is a redox pair after being conjugated and can scavenge reactive oxygen species;

wherein the conjugate has the structure of Formula (I):

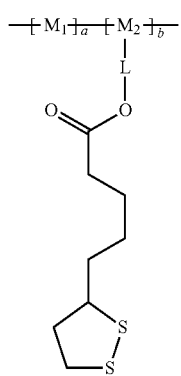

Formula (I)

where $M_1$ and $M_2$ are independently a monomer; L is a divalent linking group; and a and b represent the molar percentage of each monomer present in the polymer conjugate, where a+b=100 molar percent.

15. The method of claim 14, wherein the polymer contains sidechains having a terminal epoxy, hydroxyl, or amino group which react with lipoic acid.

16. The method of claim 14, wherein the polymer includes a first monomer selected from the group consisting of acrylates, acrylamides, silanes, and vinylphenols; and wherein the polymer includes a second monomer which is an alkene.

17. The method of claim 14, wherein the polymer is a poly(glycidyl methacrylate) polymer.

18. A method of reducing neurodegeneration around an electrode in a patient, comprising: inserting an electrode into a patient, the electrode having an outermost coating comprising a conjugate of a polymer with alpha lipoic acid, the conjugate containing free 1,2-dithiolane groups;

wherein the conjugate has the structure of Formula (I):

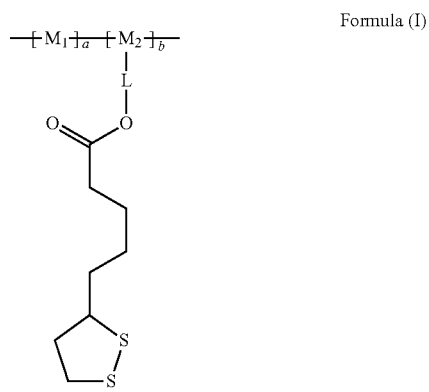

Formula (I)

where $M_1$ and $M_2$ are independently a monomer; L is a divalent linking group; and a and b represent the molar percentage of each monomer present in the polymer conjugate, where a+b=100 molar percent.

19. The method of claim 18, wherein the polymer contains sidechains having a terminal epoxy, hydroxyl, or amino group which react with the lipoic acid.

20. The method of claim 18, wherein the polymer is a poly(glycidyl methacrylate) polymer.

* * * * *